United States Patent
Betsugi et al.

(10) Patent No.: US 11,147,644 B2
(45) Date of Patent: Oct. 19, 2021

(54) STERILE DRAPE, INSTRUMENT ATTACHMENT SET FOR ATTACHING SURGICAL INSTRUMENT, AND METHOD FOR ATTACHING SURGICAL INSTRUMENT TO ROBOT ARM

(71) Applicant: MEDICAROID CORPORATION, Kobe (JP)

(72) Inventors: Shota Betsugi, Kobe (JP); Yu Usuki, Kobe (JP); Kenji Ago, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 202 days.

(21) Appl. No.: 16/537,390

(22) Filed: Aug. 9, 2019

(65) Prior Publication Data

US 2020/0069390 A1     Mar. 5, 2020

(30) Foreign Application Priority Data

Aug. 28, 2018 (JP) .............................. JP2018-159337

(51) Int. Cl.
| | | |
|---|---|---|
| *A61B 46/13* | (2016.01) | |
| *A61B 17/00* | (2006.01) | |
| *A61B 34/37* | (2016.01) | |
| *A61B 90/50* | (2016.01) | |
| *A61B 34/30* | (2016.01) | |
| *A61B 90/00* | (2016.01) | |

(52) U.S. Cl.
CPC ........ *A61B 46/13* (2016.02); *A61B 17/00234* (2013.01); *A61B 34/37* (2016.02); *A61B 90/50* (2016.02); *A61B 90/361* (2016.02); *A61B 2017/00017* (2013.01); *A61B 2017/00398* (2013.01); *A61B 2017/00477* (2013.01); *A61B 2034/305* (2016.02)

(58) Field of Classification Search
CPC . A61B 17/00; A61B 17/00234; A61B 19/201; A61B 19/203; A61B 19/5244; A61B 34/37; A61B 46/13; A61B 90/50
See application file for complete search history.

(56) References Cited

U.S. PATENT DOCUMENTS

| | | | |
|---|---|---|---|
| 4,817,592 A | * | 4/1989 | Auchinleck ............ A61G 13/12 128/855 |
| 7,727,244 B2 | | 6/2010 | Orban, III et al. |
| 8,142,447 B2 | | 3/2012 | Cooper et al. |
| 8,202,278 B2 | | 6/2012 | Orban, III et al. |
| 8,220,468 B2 | | 7/2012 | Cooper et al. |
| 8,678,009 B2 | | 3/2014 | Hagn |

(Continued)

*Primary Examiner* — Vi X Nguyen
(74) *Attorney, Agent, or Firm* — Metrolex IP Law Group, PLLC

(57) ABSTRACT

A sterile drape according to an embodiment may include: a flexible film member including a first opening and a second opening and configured to cover the robot arm received through the second opening; and a resin molded member configured to close the first opening of the flexible film member. The resin molded member includes: an upper surface portion having a shape and a size fitted to an attachment surface of an attachment portion of the robot arm; a side surface portion extending downward from the upper surface portion; and a projection which projects outward from a lower edge of the side surface portion and to which the flexible film member is welded.

12 Claims, 7 Drawing Sheets

(56) References Cited

U.S. PATENT DOCUMENTS

| | | |
|---|---|---|
| 9,320,568 B2 | 4/2016 | Orban, III et al. |
| 9,737,373 B2 | 8/2017 | Schuh |
| 2016/0081753 A1 | 3/2016 | Kostrzewski |
| 2016/0151115 A1 | 6/2016 | Karguth et al. |
| 2016/0361129 A1 | 12/2016 | Morrissette et al. |
| 2017/0086934 A1 | 3/2017 | Devengenzo et al. |
| 2017/0128142 A1* | 5/2017 | Still ................. G11C 29/36 |
| 2017/0296040 A1 | 10/2017 | Haraguchi et al. |
| 2017/0360516 A1 | 12/2017 | Hares |
| 2018/0125597 A1 | 5/2018 | Gogarty et al. |
| 2018/0132959 A1 | 5/2018 | Marshall et al. |
| 2018/0140371 A1 | 5/2018 | Hares et al. |
| 2018/0200014 A1 | 7/2018 | Bonny et al. |
| 2018/0289438 A1 | 10/2018 | Pennoyer |
| 2019/0046284 A1 | 2/2019 | Pennoyer et al. |

\* cited by examiner

STERILE DRAPE, INSTRUMENT ATTACHMENT SET FOR ATTACHING SURGICAL INSTRUMENT, AND METHOD FOR ATTACHING SURGICAL INSTRUMENT TO ROBOT ARM

CROSS-REFERENCE TO RELATED APPLICATIONS

This application claims priority to Japanese Patent Application No. 2018-159337 filed on Aug. 28, 2018, the entire contents of which are incorporated herein by reference.

TECHNICAL FIELD

One or more embodiments disclosed herein relate to sterile drapes, and particularly relate to a sterile drape including a flexible film member having an opening and a resin molded member disposed to close the opening of the flexible film member.

BACKGROUND

Sterile drapes including a flexible film member having an opening and a resin molded member disposed to close the opening of the flexible film member have been known (see, for example, U.S. Pat. No. 8,142,447).

U.S. Pat. No. 8,142,447 discloses a sterile drape including a flexible film member having an opening and a resin molded member disposed to close the opening of the flexible film member. The film member is attached to a peripheral portion of the resin molded member. The resin molded member is in a flat plate-like shape.

In a state in which a robot arm that includes an attachment portion having a plurality of drive elements is covered with the film member, the resin molded member of the sterile drape disclosed in U.S. Pat. No. 8,142,447 is sandwiched between the attachment portion and an adapter that includes a plurality of driven elements associated with the plurality of drive elements. The resin molded member is provided with a hole through which a plurality of drive elements are inserted.

SUMMARY

In attaching the sterile drape disclosed in U.S. Pat. No. 8,142,447 to the robot arm, the flat plate-like resin molded member is positioned at the attachment portion of the robot arm, and is secured by the adapter. Positioning of the resin molded member is therefore difficult.

One or more embodiments disclosed herein provide a sterile drape which facilitates positioning of a resin molded member in attachment.

A sterile drape of one or more embodiments may include a flexible film member including a first opening and a second opening and configured to cover the robot arm received through the second opening and a resin molded member configured to close the first opening of the flexible film member, wherein the resin molded member includes an upper surface portion having a shape and a size fitted to an attachment surface of the attachment portion, a side surface portion extending downward from the upper surface portion, and a projection which projects outward from a lower edge of the side surface portion and to which the flexible film member is welded, the upper surface portion, the side surface portion, and the projection being integrally formed, wherein the upper surface portion has a plurality of holes at positions corresponding to a plurality of rotating drive sections and a plurality of engagement projecting portions, the rotating drive sections and the engagement projecting portions being formed in the attachment portion, and wherein the adapter includes a plurality of rotated members which correspond to the plurality of rotating drive sections, and a plurality of engagement recesses which engage with the plurality of engagement projecting portions. The "upper surface portion" represents a concept of a plane which faces vertically upward when the resin molded member is placed on the ground with the projection of the resin molded member touching the ground.

An instrument attachment set of one or more embodiments may include an adapter including a plurality of rotated members which correspond to a plurality of rotating drive sections provided in the attachment portion, and a plurality of engagement recesses which correspond to a plurality of engagement projecting portions provided in the attachment portion, and a sterile drape including a flexible film member including a first opening and a second opening and configured to cover the robot arm received through the second opening, and a resin molded member configured to close the first opening of the flexible film member, wherein the resin molded member includes an upper surface portion having a shape and a size fitted to an attachment surface of the attachment portion, a side surface portion extending downward from the upper surface portion, and a projection which projects outward from a lower edge of the side surface portion and to which the flexible film member is welded, the upper surface portion, the side surface portion, and the projection being integrally formed, and wherein the upper surface portion has a plurality of holes which are disposed at positions that allow engagement between the plurality of rotating drive sections and the plurality of rotated members and engagement between the plurality of engagement projecting portions and the plurality of engagement recesses.

A method for attaching a surgical instrument to a robot arm used in a robotic surgical system according to one or more embodiments may include: preparing a sterile drape including a flexible film member including a first opening and a second opening and configured to cover the robot arm received through the second opening, and a resin molded member configured to close the first opening of the flexible film member; attaching the resin molded member to an attachment portion of the robot arm which is inserted from the second opening; attaching an adapter via the resin molded member attached to the attachment portion; and attaching the surgical instrument to the adapter, wherein the resin molded member includes: an upper surface portion having a shape and a size fitted to an attachment surface of the attachment portion; a side surface portion extending downward from the upper surface portion; and a projection which projects outward from a lower edge of the side surface portion and to which the flexible film member is welded, the upper surface portion, the side surface portion, and the projection being integrally formed, wherein the adapter includes a plurality of rotated members which correspond to the plurality of rotating drive sections, and a plurality of engagement recesses which engage with the plurality of engagement projecting portions, and wherein the upper surface portion has a plurality of holes which are disposed at positions that allow engagement between the plurality of rotating drive sections and the plurality of rotated members and engagement between the plurality of engagement projecting portions and the plurality of engagement recesses.

DETAILED DESCRIPTION

One or more embodiments will be described below with reference to the drawings.

(Configuration of Robotic Surgical System)

Configurations of a robotic surgical system 100 according to an embodiment will be described with reference to FIGS. 1 and 2.

Figure 1:
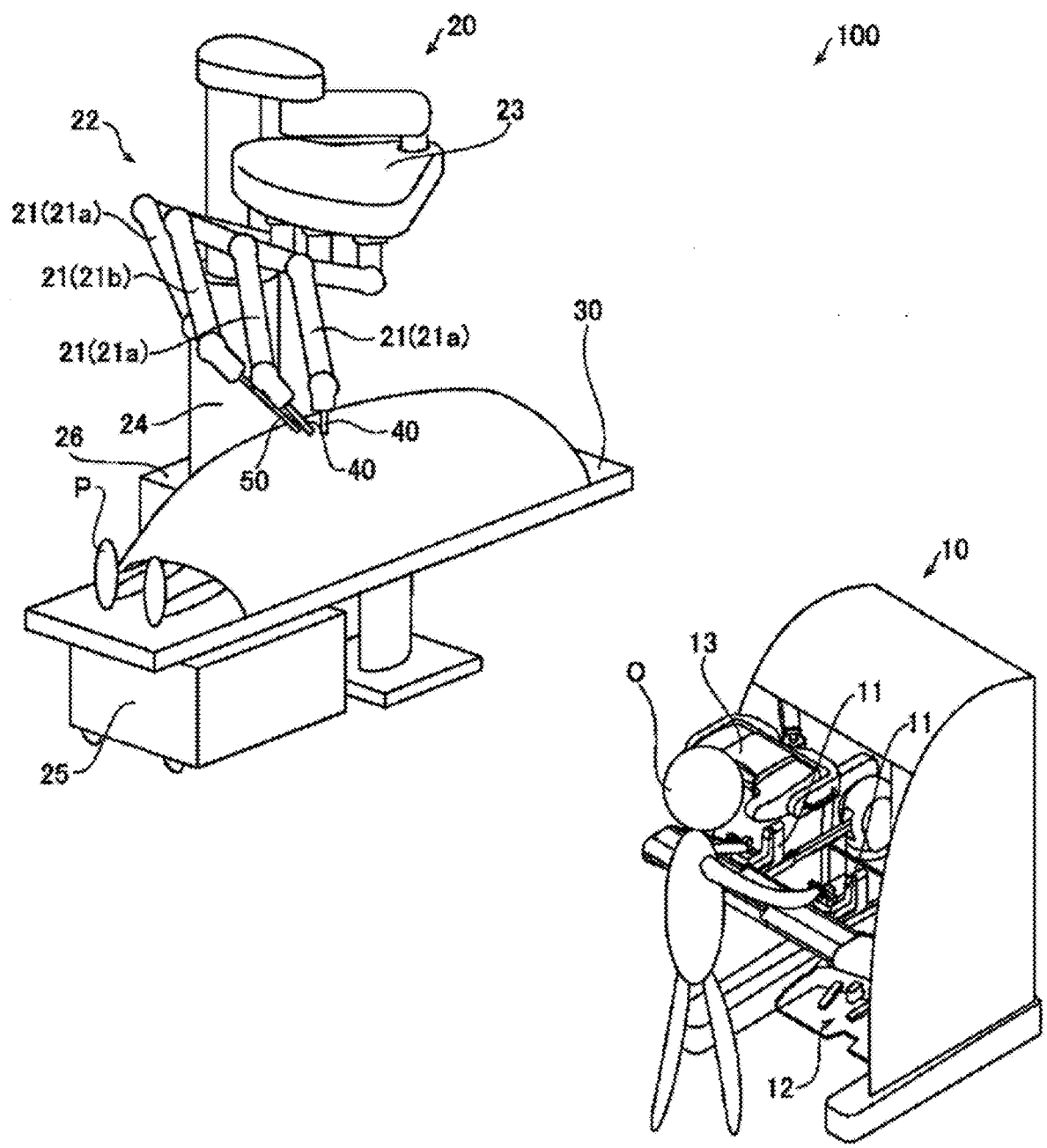
FIG. 1 is a diagram schematically illustrating a robotic surgical system according to an embodiment.

As illustrated in FIG. 1, the robotic surgical system 100 includes a remote control apparatus 10 and a patient-side apparatus 20. The remote control apparatus 10 is used to remotely operate medical equipment provided for the patient-side apparatus 20. When an operator O, who is a surgeon, enters a movement type instruction to be executed by the patient-side apparatus 20 to the remote control apparatus 10, the remote control apparatus 10 transmits the movement type instruction to the patient-side apparatus 20 via a controller 26. The patient-side apparatus 20 then handles the medical equipment, such as a surgical instrument 40 or an endoscope 50 attached to a robot arm 21, in response to the movement type instruction transmitted from the remote control apparatus 10. A minimally invasive operation is performed in this manner.

The patient-side apparatus 20 constitutes an interface through which a surgery is performed on a patient P. The patient-side apparatus 20 is arranged beside a surgical table 30 on which the patient P lies. The patient-side apparatus 20 has a plurality of robot arms 21. An endoscope 50 is attached to one of the robot arms 21 (i.e., the robot arm 21(21b)). Surgical instruments 40 are attached to the other robot arms 21(21a). The robot arms 21 are supported by the same platform 23. Each of the robot arms 21 has a plurality of joints. A driving section including a servomotor and a position detector such as an encoder are provided for each joint. Each robot arm 21 is configured to be controlled such that the medical equipment attached to the robot arm 21 makes a desired movement in response to a driving signal given via the controller 26.

The platform 23 is supported by a positioner 22 placed on the floor of the operating room. The positioner 22 includes a column 24 having a lifting shaft adjustable in a vertical direction, and the lifting shaft is coupled to a base 25 having wheels and movable on the floor surface.

The surgical instrument 40 as the medical equipment is detachably attached to a distal end portion of the robot arm 21a. The surgical instrument 40 includes a housing 43 (see FIG. 4) attached to the robot arm 21a, an elongated shaft 42 (see FIG. 4), and an end effector 41 (see FIG. 4) attached to a distal end portion of the shaft 42. Examples of the end effector 41 include, but are not limited to, a grasping forceps, scissors, a hook, a high-frequency knife, a snare wire, a clamp, and a stapler, and may include various types of treatment tools. In a surgery using the patient-side apparatus 20, each of the robot arms 21a introduces the surgical instrument 40 into the body of the patient P through a cannula (a trocar) retained on the body surface of the patient P. The end effector 41 of the surgical instrument 40 is placed in the vicinity of the surgical site.

The endoscope 50 as the medical equipment is detachably attached to a distal end portion of the robot arm 21b. The endoscope 50 takes images in the body cavity of the patient P. The images taken are output to the remote control apparatus 10. Examples of the endoscope 50 include a 3D endoscope capable of taking three-dimensional images, or a 2D endoscope. In a surgery using the patient-side apparatus 20, the robot arm 21b introduces the endoscope 50 into the body of the patient P through a trocar retained on the body surface of the patient P. The endoscope 50 is placed in the vicinity of the surgical site.

The remote control apparatus 10 constitutes an interface with the operator O. The remote control apparatus 10 serves as a device through which the operator O operates the medical equipment attached to each robot arm 21. That is, the remote control apparatus 10 is configured to be capable of transmitting, to the patient-side apparatus 20, the movement type instruction that has been input by the operator O and that should be executed by the surgical instrument 40 and the endoscope 50, via the controller 26. The remote control apparatus 10 is installed beside the surgical table 30 so that the operator can check the condition of the patient P while operating the master, for example. The remote control apparatus 10 may be configured, for example, to wirelessly transmit the movement type instruction, and may be installed in a room different from the operating room where the surgical table 30 is placed.

The term "movement type" to be performed by the surgical instrument 40 may refer to the type of movement (a series of positions and orientations) of the surgical instrument 40 and the type of movement executed by the function of the respective surgical instruments 40. For example, if the surgical instrument 40 is a grasping forceps, the movement type to be performed by the surgical instrument 40 includes positions of rolling and pitching of a wrist of the end effector 41, and opening and closing the jaws. If the surgical instrument 40 is a high-frequency knife, the movement type to be executed by the surgical instrument 40 may include vibration of the high-frequency knife, specifically, a current supply to the high-frequency knife. If the surgical instrument 40 is a snare wire, the movement type to be performed by the surgical instrument 40 may include tightening, and releasing from the tightening. In addition, the movement type may include a movement of burning off a target site of the surgery, using a bipolar or a monopolar to which an electric current is supplied.

Examples of the movement type to be performed by the endoscope 50 include positioning, and determination of the orientation, of the tip end of the endoscope 50, or setting of zoom magnification of the endoscope 50.

Figure 2:
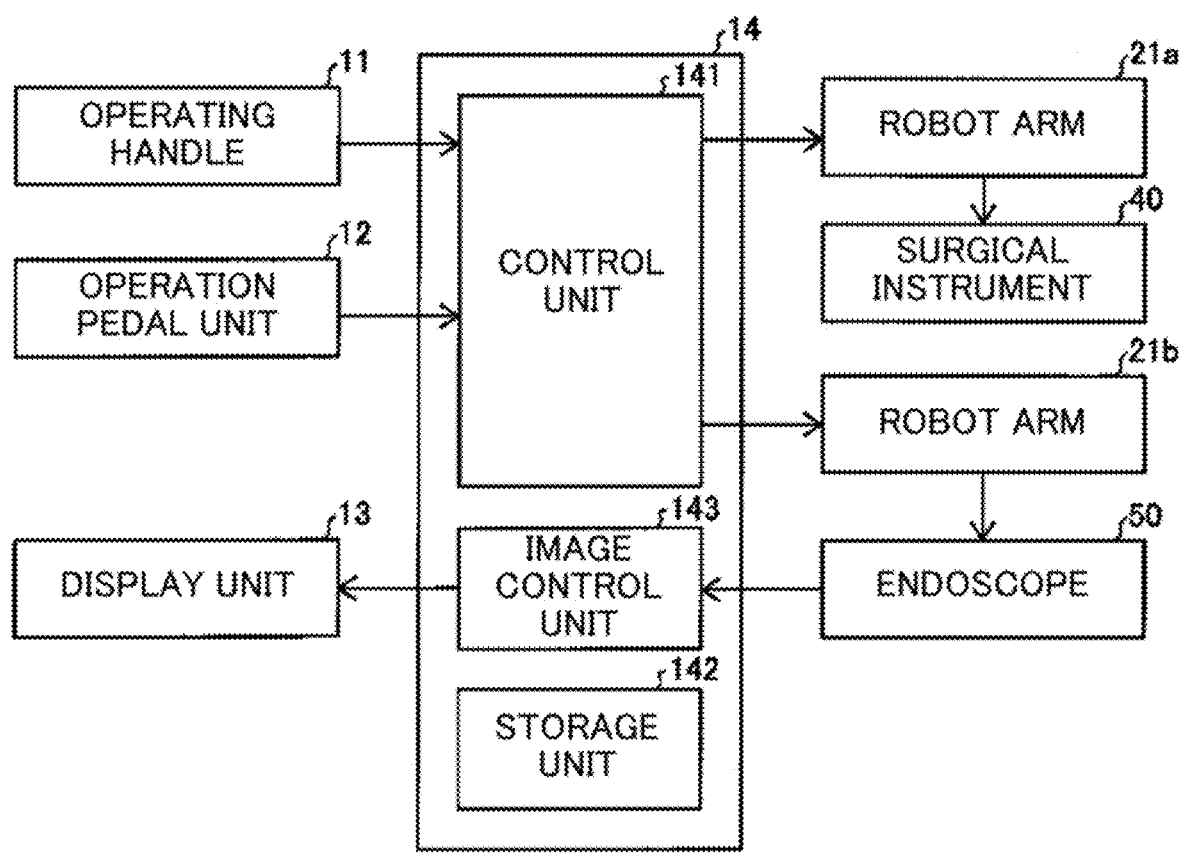
FIG. 2 is a block diagram illustrating a control configuration of the robotic surgical system according to an embodiment.

As illustrated in FIGS. 1 and 2, the remote control apparatus 10 includes an operating handle 11, an operation pedal unit 12, a display unit 13, and a control device 14.

The operating handle 11 is intended to remotely operate the medical equipment attached to each robot arm 21. Specifically, the operating handle 11 accepts the operation conducted by the operator O to control the medical equipment (i.e., the surgical instrument 40 and the endoscope 50). The operating handle 11 includes two operating handles 11 arranged in the horizontal direction. Specifically, one of the two operating handles 11 is operated by the right hand of the operator O, and the other operating handle 11 is operated by the left hand of the operator O.

The operating handle 11 is arranged to extend from the back side to the front side of the remote control apparatus 10. The operating handle 11 is configured to be movable within a predetermined three-dimensional operation area A. Specifically, the operating handle 11 is configured to be movable up and down directions, the leftward and rightward directions, and the forward and backward directions.

The remote control apparatus 10 and the patient-side apparatus 20 constitute a master-slave system in controlling the movements of the robot arms 21a and the robot arm 21b. Specifically, the operating handle 11 serves as a master controlling element in the master-slave system, and the robot arms 21a and the robot arm 21b to which the medical equipment is attached serve as slave moving elements. When the operator O operates the operating handle 11, the movement of the robot arms 21a or the robot arm 21b is controlled so that the distal end portion of each robot arm 21a (i.e., the end effector 41 of surgical instrument 40) or the distal end portion of the robot arm 21b (i.e., the endoscope 50) will trace the movement of the operating handle 11 and shift accordingly.

The patient-side apparatus 20 is configured to control the movements of the respective robot arms 21a according to a movement scale factor which has been set. For example, in a case in which the movement scale factor has been set to be ½, the end effector 41 of the surgical instrument 40 is controlled to shift by one half (½) of a distance by which the operating handle 11 has shifted. As a result, precise surgery can be accurately performed.

The operation pedal unit 12 includes a plurality of pedals for executing the function related to the medical equipment. The plurality of pedals include a coagulation pedal, a cutting pedal, a camera pedal, and a clutch pedal. The plurality of pedals are operated by the foot of the operator O.

The coagulation pedal enables the operation of coagulating the surgical site using the surgical instrument 40. Specifically, when the coagulation pedal is operated, a voltage for coagulation is applied to the surgical instrument 40, thereby coagulating the surgical site. The cutting pedal enables the operation of cutting the surgical site using the surgical instrument 40. Specifically, when the cutting pedal is operated, a voltage for the cutting is applied to the surgical instrument 40, thereby cutting the surgical site.

The camera pedal is used to change the position and orientation of the endoscope 50 taking images of the body cavity. Specifically, the camera pedal validates the operation of the endoscope 50 through the operating handle 11. That is, while the camera pedal is pressed down, the position and orientation of the endoscope 50 can be changed by using the operating handle 11. For example, the endoscope 50 is operated using both of the left and right operating handles 11. Specifically, the endoscope 50 rotates when the right and left operating handles 11 rotate about a midpoint between the left and right operating handles 11. The endoscope 50 moves forward when the left and right operating handles 11 are pushed forward. The endoscope 50 moves backward when the left and right operating handles 11 are pulled backward. The endoscope 50 moves up and down, and leftward and rightward when the left and right operating handles 11 are moved up and down, and leftward and rightward.

The clutch pedal is used to temporarily block the connection for operation between the robot arm 21 and the operating handle 11 to stop the movement of the surgical instrument 40. Specifically, while the clutch pedal is pressed down, the robot arm 21 of the patient-side apparatus 20 does not move even if the operating handle 11 is moved. For example, when the operating handle 11 comes close to the end of the movable range thereof, the clutch pedal is pressed down to temporarily block the connection for operation so that the operating handle 11 can be returned to the center position. When the clutch pedal is no longer pressed down, the robot arm 21 and the operating handle 11 are connected again, and the operating handle 11 can be operated again at around the center position.

The display unit 13 can display the images taken by the endoscope 50. The display unit 13 includes a scope type display unit or a non-scope type display unit. The scope type display unit is, for example, a display unit which an operator looks into. The non-scope type display unit represents a concept that includes an open display unit having a flat screen which an operator does not look into, just like a display of a common personal computer.

In a case in which the scope type display unit is attached, a 3D image taken by the endoscope 50 attached to the robot arm 21b of the patient-side apparatus 20 is displayed. Also in a case in which the non-scope type display unit is attached, a 3D image taken by the endoscope 50 provided in the patient-side apparatus 20 is displayed. In the case in which the non-scope type display unit is attached, a 2D image taken by the endoscope 50 provided in the patient-side apparatus 20 may be displayed.

As illustrated in FIG. 2, the control device 14 includes, for example, the control unit 141 including an arithmetic unit such as a CPU, a storage unit 142 including a memory such as a ROM and a RAM, and an image control unit 143. The control device 14 may be comprised of a single controller which provides centralized control, or may be configured as a plurality of controllers which work in cooperation with each other and provide distributed control. The control unit 141 determines whether the movement type instruction input through the operating handle 11 is a movement type instruction to be executed by the robot arm 21a, or a movement type instruction to be executed by the endoscope 50, in accordance with the state of the operation pedal unit 12. If the control unit 141 determines that the movement type instruction input through the operating handle 11 is a movement type instruction to be executed by the surgical instrument 40, the control unit 141 transmits this movement type instruction to the robot arm 21a. In response, the robot arm 21a is driven, as a result of which the operation of the surgical instrument 40 attached to the robot arm 21a is controlled.

Alternatively, if the control unit 141 determines that the movement type instruction input through the operating handle 11 is a movement type instruction to be executed by the endoscope 50, the control unit 141 transmits the movement type instruction to the robot arm 21b. In response, the robot arm 21b is driven, as a result of which the operation of the endoscope 50 attached to the robot arm 21b is controlled.

The storage unit 142 stores, for example, control programs corresponding to the types of the surgical instrument 40. The control unit 141 reads the control program in accordance with the type of the surgical instrument 40 attached, thereby allowing the movement instruction entered through the operating handle 11 and/or operation pedal unit 12 of the remote control apparatus 10 to cause each surgical instrument 40 to perform a suitable operation.

The image control unit 143 transmits images taken by the endoscope 50 to the display unit 13. The image control unit 143 processes or corrects the image as needed.

(Configurations of Adapter and Attachment Portion)

Configurations of an adapter 60 and an attachment portion 211 according to an embodiment will be described with reference to FIGS. 3 to 11.

Figure 3:
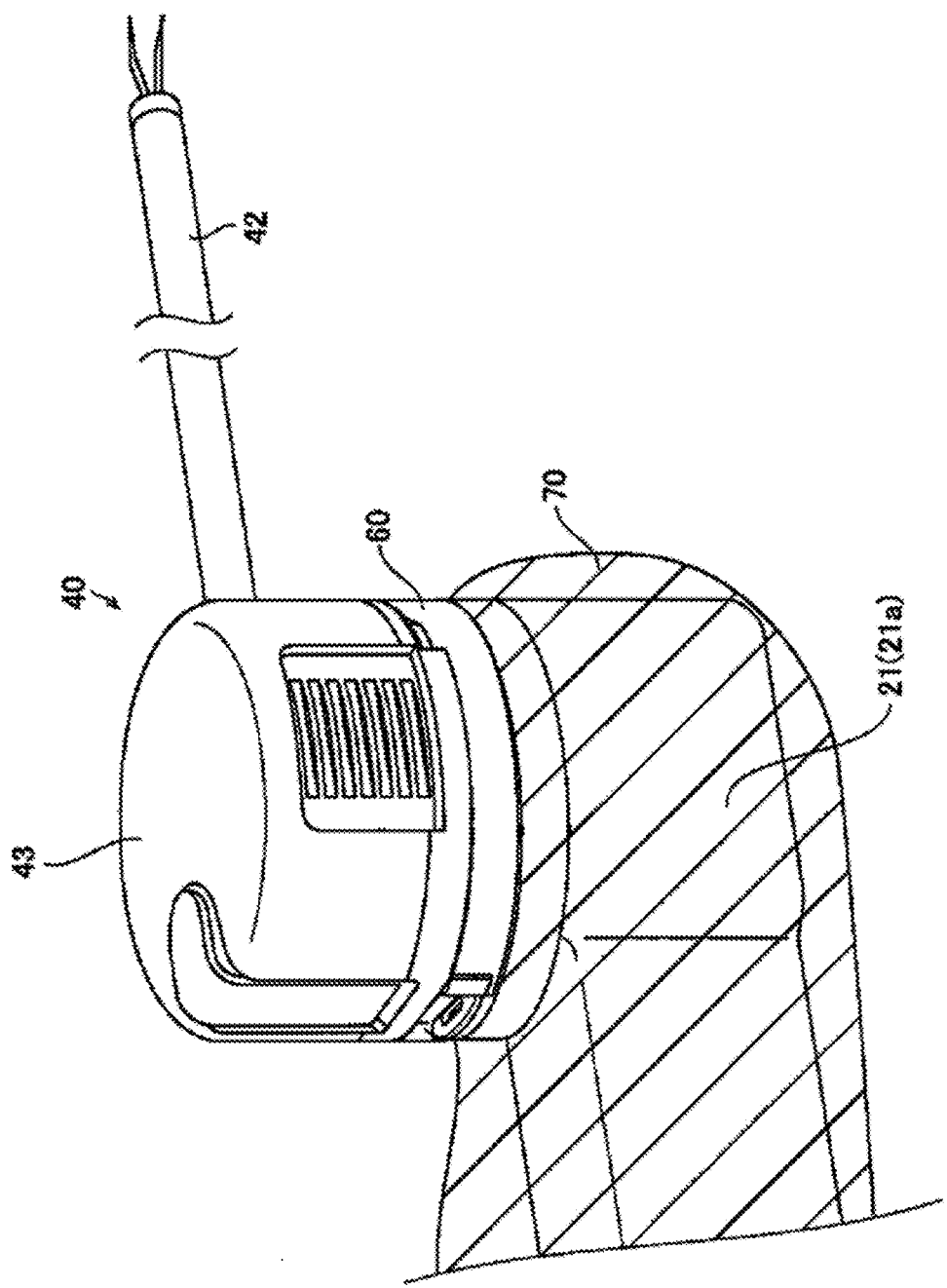
FIG. 3 is a diagram illustrating a perspective view of the state in which a surgical instrument is attached to a robot arm according to an embodiment via an adapter.

As illustrated in FIG. 3, the robot arm 21 is covered with a drape 70 because the robot arm 21 is used in a clean zone. In an operating room, a cleaning procedure is carried out to prevent surgery incisions and medical equipment from being infected and contaminated with pathogenic bacteria or foreign substances. A clean zone and a contaminated zone, which is a zone other than the clean zone, are defined in this cleaning procedure. The surgical site is positioned in the clean zone. Surgery team members, including the operator O, take good care so that only a disinfected object is placed in the clean zone during the surgery, and sterilize the object placed in the contaminated zone when it needs to be moved to the clean zone. Similarly, if the surgery team members, including the operator O, have put their hands in the contaminated zone, they sterilize their hands before they directly touch an object placed in the clean zone. The instrument to be used in the clean zone is sterilized, or is covered with a sterilized drape 70. The drape 70 is an example of a "sterile drape" recited in the claims.

<Attachment Portion>

Figure 4:
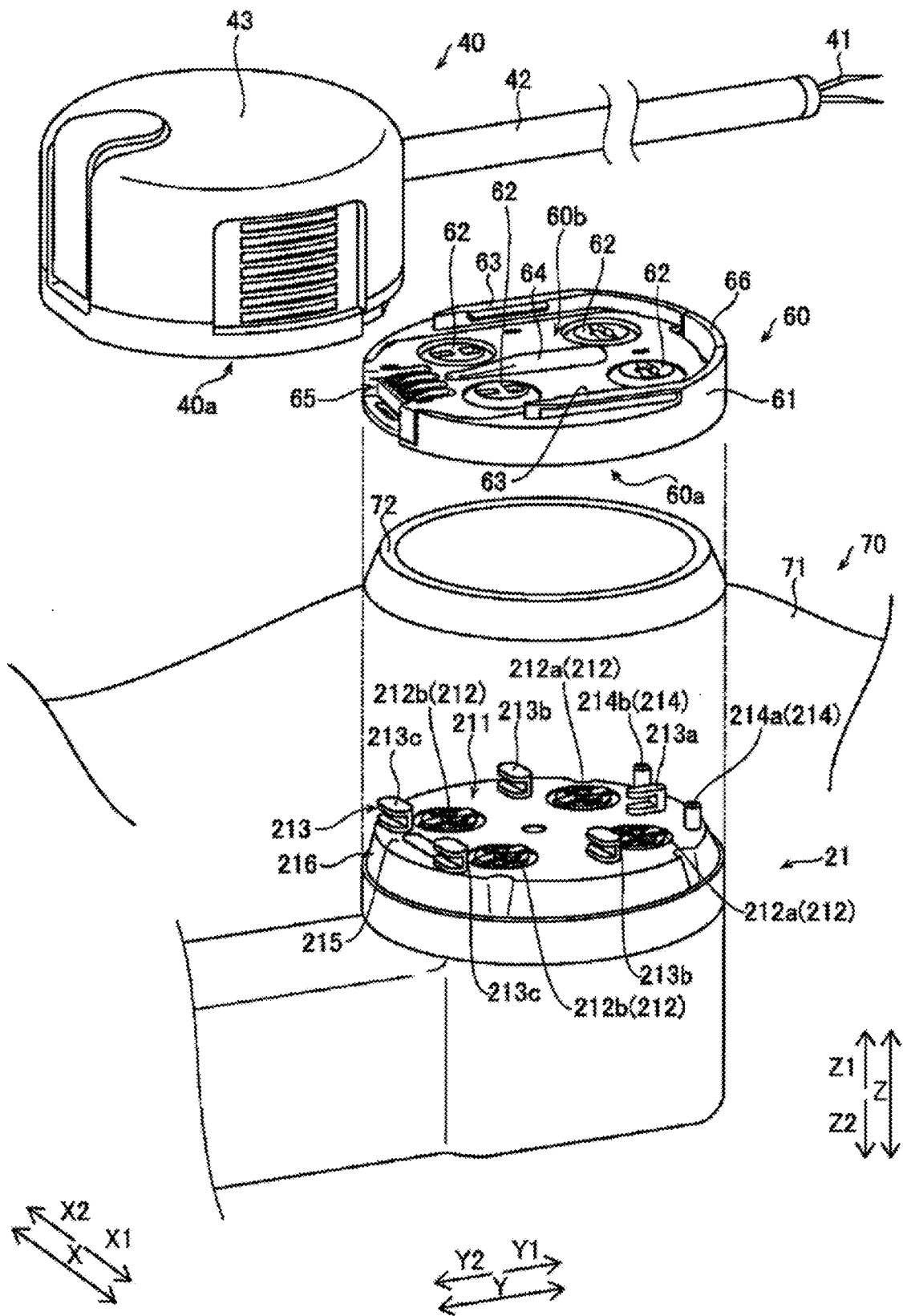
FIG. 4 is a diagram illustrating a perspective view of the state in which the surgical instrument and the adapter are detached from the robot arm according to an embodiment.

As illustrated in FIG. 4, the robot arm 21 includes an attachment portion 211 having an attachment surface 215 and an attachment side surface 216, a driving member 212, an engagement projecting portion 213, and a boss 214. The direction in which the attachment portion 211 and the adapter 60 are arranged is referred to as Z direction. One of the Z direction is referred to as Z1 direction, and the other is referred to as Z2 direction. The direction in which the robot arm 21 extends is referred to as Y direction. One of the Y direction is referred to as Y1 direction, and the other is referred to as Y2 direction. The Z direction and the Y direction are orthogonal to each other. The direction orthogonal to the Z and Y directions is referred to as X direction. One of the X direction is referred to as X1 direction, and the other is referred to as X2 direction. The Z2 direction is an example of "downward" recited in the claims. The Z direction is an example of a "vertical direction" recited in the claims. The X direction and the Y direction are an example of a "horizontal direction" recited in the claims. The boss 214 is an example of an "engagement projecting portion" recited in the claims.

The attachment surface 215 is a surface of the attachment portion 211 toward the Z1 direction. The attachment surface 215 has approximately a circular shape when viewed from the Z1 direction. The attachment side surface 216 extends from the attachment surface 215 in the Z2 direction. Specifically, the attachment side surface 216 is an inclined surface that inclines outward in the radial direction of the attachment surface 215 from a peripheral portion of the attachment surface 215 toward the Z2 direction. The attachment surface 215 and the attachment side surface 216 of the attachment portion 211 toward the Z1 direction has approximately a circular truncated cone shape when viewed from the X1 direction.

Each of the driving member 212, the engagement projecting portion 213, and the boss 214 is provided on the attachment surface 215. The driving member 212 rotates about rotational axis extending in the Z direction. The driving member 212 includes two first driving members 212a and two second driving members 212b. In the attachment surface 215, the two first driving members 212a and the two second driving members 212b are arranged sequentially in the Y2 direction. The driving member 212 is an example of a "rotating drive section" recited in the claims.

The engagement projecting portion 213 includes a first engagement projecting portion 213a, two second engagement projecting portions 213b, and two third engagement projecting portions 213c. In the attachment surface 215, the first engagement projecting portion 213a, the two second engagement projecting portions 213b, and the two third engagement projecting portions 213c are arranged sequentially in the Y2 direction. Each of the first engagement projecting portion 213a, the two second engagement projecting portions 213b, and the two third engagement projecting portions 213c protrudes in the Z1 direction. The engagement projecting portion 213 is intended to engage with a plurality of recesses 67 (see FIG. 5) of the adapter 60, which will be described later.

The boss 214 includes a first boss 214a and a second boss 214b. The first boss 214a and the second boss 214b are disposed in a portion on the attachment surface 215 toward the Y1 direction. The first boss 214a is disposed on the side toward X1 direction with respect to the second boss 214b. The first boss 214a and the second boss 214b are opposed to each other in the X direction. The adapter 60 is attached to the attachment portion 211 of the robot arm 21. The first boss 214a and the second boss 214b protrude in the Z1 direction.

<Adapter>

The surgical instrument 40 is attached to the adapter 60. The robot arm 21 transmits power to the surgical instrument 40 via the adapter 60 in order to drive the end effector 41 of the surgical instrument 40.

Figure 5:
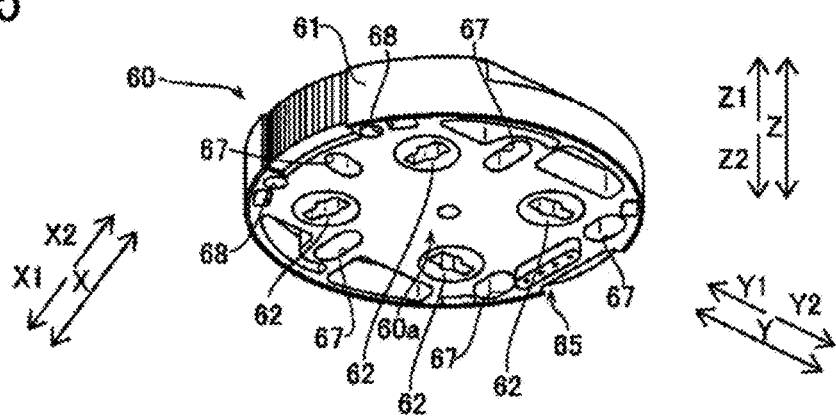
FIG. 5 is a diagram illustrating a perspective view of the adapter according to an embodiment as viewed from below.

The adapter 60 includes a base 61, a plurality of drive power transmission members 62, a guide rail 63, a leading guide rail 64, an electrode array 65, and an arm engagement member 66. As illustrated in FIG. 5, the adapter 60 includes a plurality of recesses 67 and a plurality of positioning holes 68. The drive power transmission members 62 are an example of a "rotated member" recited in the claims. The recesses 67 are an example of an "engagement recess" recited in the claims.

As illustrated in FIGS. 4 and 5, a first surface 60a of the adapter 60 toward the Z2 direction is attached to the robot arm 21. The surgical instrument 40 is attached to a second surface 60b of the adapter 60 toward the Z1 direction. An attachment surface 40a of the housing 43 of the surgical instrument 40 toward the Z2 direction is attached to the adapter 60.

The plurality of drive power transmission members 62 are associated with the respective driving members 212. The plurality of recesses 67 are associated with the respective engagement projecting portions 213.

The drive power transmission members 62 are rotatably disposed in the base 61. Specifically, the drive power transmission members 62 are rotatable about a rotational axis extending in the Z direction. The drive power transmission members 62 transmit the rotation of the plurality of driving members 212, which are provided for the attachment portion 211 of the robot arm 21a, to the plurality of driven sections (not shown) provided for the surgical instrument 40. A multiple number of drive power transmission members 62 are provided so as to correspond to the respective driving members 212 of the robot arm 21a and the respective driven sections (not shown) provided for the surgical instrument 40. The plurality of drive power transmission members 62 are disposed at positions corresponding to the respective driving members 212 of the robot arm 21a and the respective driven sections (not shown) of the surgical instrument 40.

The positioning holes 68 are formed in the first surface 60a. The bosses 214 of the robot arm 21 are fitted in the positioning holes 68. A multiple number of positioning holes 68 are formed. The plurality of positioning holes 68 are associated with the respective bosses 214. The positioning holes 68 are provided in the vicinity of an edge of the first surface 60a toward the Y1 direction.

(Drape)

Figure 6:
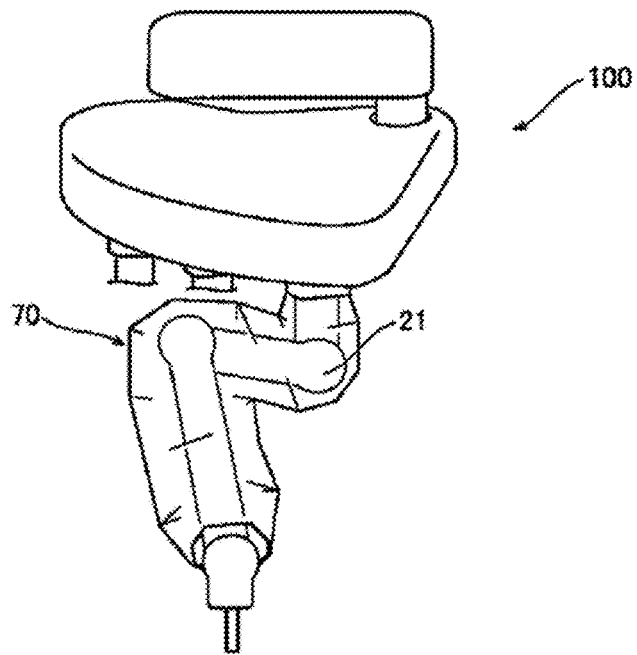
FIG. 6 is a diagram illustrating a perspective view of the state in which a drape is attached to the robot arm according to an embodiment.
Figure 7:
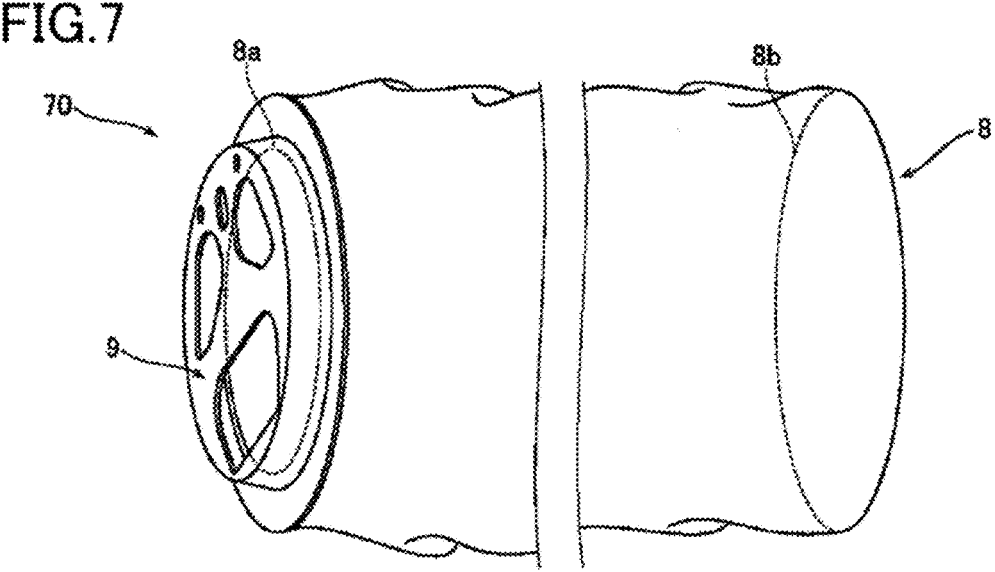
FIG. 7 is a diagram illustrating a perspective view of the drape according to an embodiment.

As illustrated in FIG. 6, the drape 70 is configured to cover the robot arm 21 used in the robotic surgical system 100. Specifically, as illustrated in FIG. 7, the drape 70 is configured to receive the robot arm 21, and includes a flexible film member 8 having an attachment opening 8a, and a resin molded member 9 provided to close the attachment opening 8a of the flexible film member 8. The attachment opening 8a is an example of a "first opening" recited in the claims.

<Flexible Film Member>

The flexible film member 8 has the above-mentioned attachment opening 8a at one end, and an insertion opening 8b at the other end. That is, the flexible film member 8 has a sleeve-like shape, with one end open by the attachment opening 8a and the other end open by the insertion opening 8b. The flexible film member 8 is made of a resin material such as thermoplastic polyurethane or polyethylene. The flexible film member 8 is formed to be like a thin film.

The attachment opening 8a has approximately a circular shape when viewed from the resin molded member 9 side. The diameter of the attachment opening 8a corresponds to the size of the resin molded member 9. The resin molded member 9 is welded to the entire peripheral portion of the attachment opening 8a. The insertion opening 8b has approximately a circular shape when viewed from the side opposite to the resin molded member 9. The diameter of the insertion opening 8b is larger than that of attachment opening 8a. The insertion opening 8b is large enough to receive the robot arm 21 into the flexible film member 8.

<Resin Molded Member>

Figure 8:
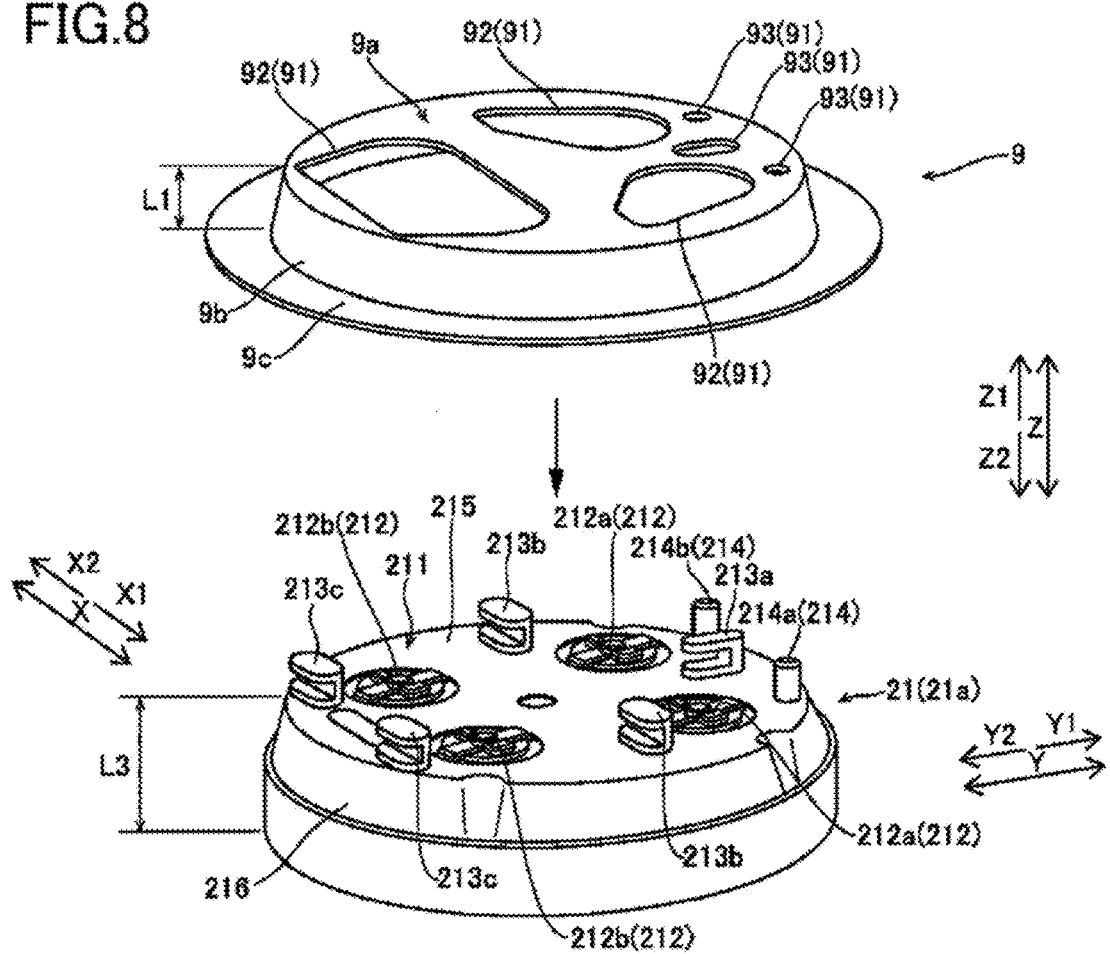
FIG. 8 is a diagram illustrating a perspective view of the state in which a resin molded member is about to be attached to an attachment portion according to an embodiment.

As illustrated in FIG. 8, the resin molded member 9 of an embodiment has a shape corresponding to the contour of the attachment portion 211. Specifically, the resin molded member 9 includes an upper surface portion 9a having a shape and a size fitted to the attachment surface 215 of the attachment portion 211, a side surface portion 9b extending from the upper surface portion 9a in the Z2 direction, and a projection 9c which projects outward from the edge, in the Z2 direction, of the side surface portion 9b (i.e., the lower edge) and to which the flexible film member 8 is welded. These portions are integrally formed.

The resin molded member 9 is properly positioned by the upper surface portion 9a and the side surface portion 9b by simply attaching the resin molded member 9 to the attachment portion 211 of the robot arm 21. This configuration facilitates the positioning of the resin molded member 9 in attachment. In addition, the movement of the resin molded member 9 associated with the movement of the robot arm 21 is restricted by the side surface portion 9b extending downward from the upper surface portion 9a which has the shape and size fitted to the attachment surface 215 of the attachment portion 211. Misalignment of the resin molded member 9 can thus be reduced. Further, the projection 9c facilitates the welding of the resin molded member 9 and the flexible film member 8 to each other.

The upper surface portion 9a and the side surface portion 9b of the resin molded member 9 have the shape and size corresponding to the attachment surface 215 of the attachment portion 211 and the attachment side surface 216 extending downward from the attachment surface 215, respectively. Thus, even when the resin molded member 9 is about to make a relative movement with respect to the attachment portion 211 of the robot arm 21, misalignment of the resin molded member 9 is less likely to occur because the side surface portion 9b of the resin molded member 9 is in contact with the attachment side surface 216 of the attachment portion 211 of the robot arm 21.

Specifically, the upper surface portion 9a and the side surface portion 9b of the resin molded member 9 form approximately a circular truncated cone shape when viewed from the X1 direction. This configuration allows the resin molded member 9 to have a shape that is more fitted to the attachment portion 211 of the robot arm 21. Misalignment of the resin molded member 9 can thus be reduced more reliably.

The resin molded member 9 is made of a resin material such as polyethylene terephthalate. The resin molded member 9 has a flat plate-like shape.

<Upper Surface Portion>

Similarly to the attachment surface 215 of the attachment portion 211, the upper surface portion 9a has approximately a circular shape when viewed from the Z1 direction. The diameter of the upper surface portion 9a is substantially the same as the diameter of the attachment surface 215 of the attachment portion 211. Thus, the upper surface portion 9a is layered on (overlaps with) the attachment surface 215 of the attachment portion 211 when viewed from the Z1 direction. As illustrated in FIG. 4, the upper surface portion 9a (see FIG. 8) is sandwiched between the adapter 60 and the attachment portion 211 of the robot arm 21. On the other hand, the side surface portion 9b (see FIG. 8) and the projection 9c (see FIG. 8) are not sandwiched between the adapter 60 and the attachment portion 211 of the robot arm 21.

<Insertion Through Hole>

Figure 9:
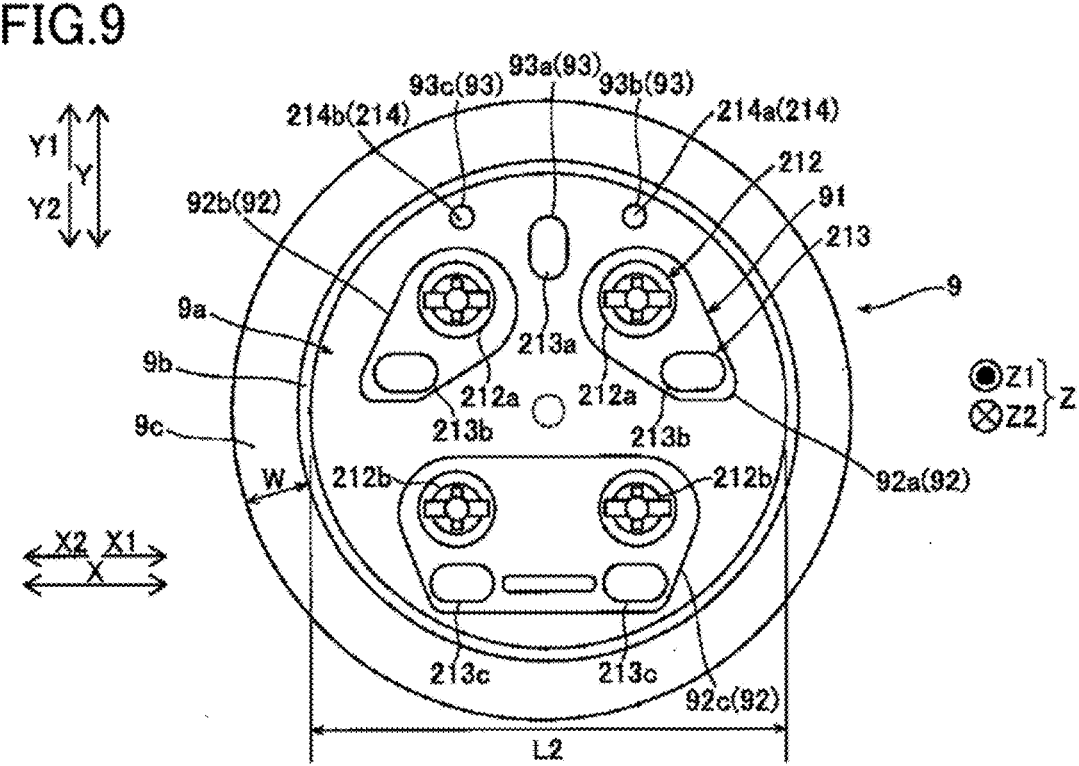
FIG. 9 is a diagram illustrating a plan view of the state in which the resin molded member is attached to the attachment portion according to an embodiment.

As illustrated in FIG. 9, the upper surface portion 9a has a plurality (i.e., six) of insertion through holes 91 at positions corresponding to the plurality (i.e., four) of the driving members 212, the plurality (i.e., five) of engagement projecting portions 213, and the plurality (i.e., two) of bosses 214. That is, the insertion through holes 91 are formed in the upper surface portion 9a so as to correspond to the two first driving members 212a, two second driving members 212b, the first engagement projecting portion 213a, two second engagement projecting portions 213b, and two third engagement projecting portions 213c. The insertion through holes 91 are formed in the upper surface portion 9a so as to further correspond to the first boss 214a and the second boss 214b.

This configuration contributes to reducing the area of a portion of the upper surface portion 9a of the resin molded member 9 where the insertion through holes 91 are formed, compared to the case in which the resin molded member 9 is provided with one insertion through hole to receive all of the plurality of driving members 212, the plurality of engagement projecting portions 213, and the plurality of bosses 214. It is therefore possible to substantially prevent a decrease in the strength of the resin molded member 9.

The plurality of insertion through holes 91 include a shared hole 92 which corresponds to both of at least one of the plurality of driving members 212 and at least one of the plurality of engagement projecting portions 213. That is, the shared hole 92 is a hole used in common to receive both of the driving member 212 and the engagement projecting portion 213. The shared hole 92 formed in the upper surface portion 9a of the resin molded member 9 contributes to reducing the number of insertion through holes 91 formed in the upper surface portion 9a of the resin molded member 9, which facilitates the fabrication of the resin molded member 9.

Specifically, the shared hole 92 includes a first shared hole 92a corresponding to one of the two first driving members 212a toward the X1 direction and one of the two second engagement projecting portions 213b toward the X1 direction. The shared hole 92 includes a second shared hole 92b corresponding to one of the two first driving members 212a toward the X2 direction and one of the two second engagement projecting portions 213b toward the X2 direction. The shared hole 92 includes a third shared hole 92c corresponding to the two second driving members 212b and the two third engagement projecting portions 213c.

The plurality of insertion through holes 91 include dedicated holes 93 which respectively correspond to one of the plurality of engagement projecting portions 213 and one of the plurality of bosses 214. That is, the dedicated holes 93 are holes used to receive the respective engagement projecting portions 213 and the bosses 214 independently from each other. The dedicated holes 93 formed in the upper surface portion 9a of the resin molded member 9 in addition to the shared hole 92 contribute to reducing an increase in complexity of the shape of the respective insertion through holes 91 formed in the upper surface portion 9a of the resin molded member 9. It is therefore possible to facilitate the fabrication of the resin molded member 9.

Specifically, the dedicated holes 93 include a first dedicated hole 93a corresponding to the first engagement projecting portion 213a. The dedicated holes 93 include a second dedicated hole 93b corresponding to the first boss 214a. The dedicated holes 93 include a third dedicated hole 93c corresponding to the second boss 214b.

The total number of the plurality (i.e., four) of driving members 212, the plurality (i.e., five) of engagement projecting portions 213, and the plurality (i.e., two) of bosses 214 is 11. The number of the plurality (i.e., six) of insertion through holes 91 is 6. That is, the number of the plurality of insertion through holes 91 is less than the total number of the plurality of driving members 212, the plurality of engagement projecting portions 213, and the plurality of bosses 214. It is therefore possible to fabricate the resin molded member 9 more easily than in the case in which the plurality of insertion through holes 91 corresponding to the total number of the plurality of driving members 212 and the plurality of engagement projecting portions 213 are formed in the upper surface portion 9a.

<Side Surface Portion>

As illustrated in FIGS. 8 and 9, the side surface portion 9b has substantially an annular shape when viewed from the Z1 direction. The side surface portion 9b is provided along the entire peripheral portion of the upper surface portion 9a. The side surface portion 9b is an inclined surface that inclines inward in the radial direction of the upper surface portion 9a toward the Z1 direction, as viewed from the X1 direction. That is, the edge of the side surface portion 9b toward the Z1 direction is inside the edge of the side surface portion 9b toward the Z2 direction with respect to the radial direction of the upper surface portion 9a.

The length L1 of the side surface portion 9b along the vertical direction is smaller than the diameter of the upper surface portion 9a. Specifically, the length L1 of the side surface portion 9b along the vertical direction is one sixth (1/6) or more and a half (1/2) or less of the maximum length L2 of the upper surface portion 9a in the X direction (Y direction). The length L1 of the side surface portion 9b along the vertical direction is the distance in the Z direction between the edge of the side surface portion 9b toward the Z2 direction and the edge of the side surface portion 9b toward the Z1 direction. This configuration makes the resin molded member 9 have a flat shape, which means that the resin molded member 9 can be compact in size in the vertical direction. The space for accommodating the drape 70 can thus be reduced.

The length L1 of the side surface portion 9b along the vertical direction is approximately a half of the length L3 of the attachment portion 211 in the Z direction.

<Projection>

As illustrated in FIGS. 8 and 9, the projection 9c has substantially an annular shape when viewed from the Z1 direction. The projection 9c protrudes outward in the radial direction of the upper surface portion 9a from the side surface portion 9b. The projection 9c is provided along the entire peripheral portion of the edge of the side surface portion 9b toward the Z2 direction. The projection 9c has a predetermined width W in the radial direction of the upper surface portion 9a. The predetermined width W is large enough to weld the rim of the attachment opening 8a of the flexible film member 8.

<Attachment Tool>

Figure 10:
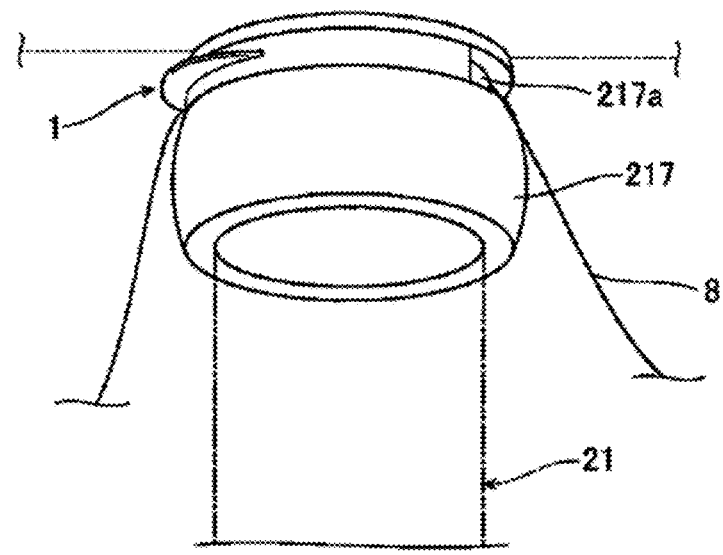
FIG. 10 is a diagram illustrating a schematic view of the state in which an attachment tool according to an embodiment is attached to a proximal end portion of the robot arm.

As illustrated in FIG. 10, the flexible film member 8 is attached to the proximal end portion 217 of the robot arm 21 by the attachment tool 1. This configuration makes it less likely that the attachment tool 1 inhibits the movement of the joints of the robot arm 21, as compared to the case in which the attachment tool 1 is attached to a position other than the proximal end portion 217 of the robot arm 21, thereby making it possible to maintain the appropriate movement of the robot arm 21.

Figure 11:
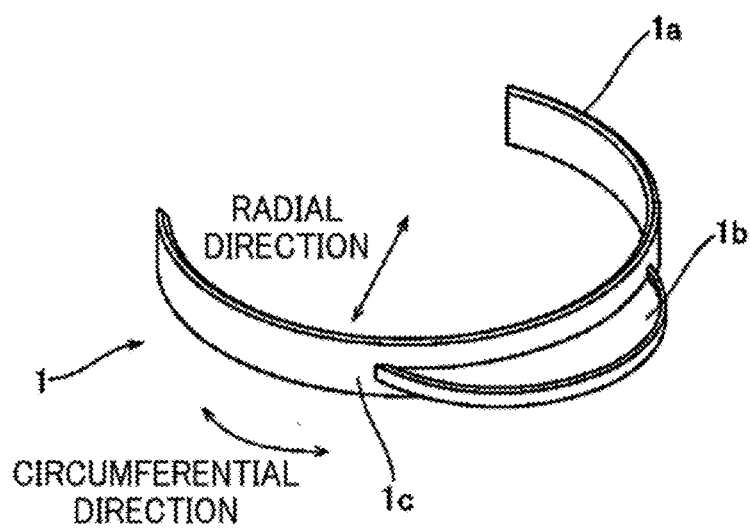
FIG. 11 is a diagram illustrating a perspective view of the attachment tool according to an embodiment.

Specifically, as illustrated in FIGS. 10 and 11, the attachment tool 1 includes an insertion portion 1a to be fitted in a groove 217a formed in the proximal end portion 217 of the robot arm 21, and a knob 1b for attaching and detaching the insertion portion 1a to and from the groove 217a formed in the proximal end portion 217 of the robot arm 21. The insertion portion 1a has approximately an arc shape along the groove 217a formed in the proximal end portion 217 of the robot arm 21. The knob 1b protrudes outward in the radial direction of the insertion portion 1a from an outer circumferential surface 1c in the radial direction of the insertion portion 1a. The knob 1b is arranged in the middle, in the circumferential direction, of the insertion portion 1a on the outer circumferential surface 1c in the radial direction of the insertion portion 1a.

The insertion portion 1a and the knob 1b are formed integrally. The insertion portion 1a and the knob 1b are made of resin.

(Variations)

One or more embodiments disclosed herein are meant to be illustrative in all respects and should not be construed to be limiting in any manner. The scope of one or more embodiments disclosed herein is defined not by the above-described embodiments, but by the scope of claims, and includes all modifications (variations) within equivalent meaning and scope to those of the claims.

For example, an example in which the dedicated holes 93 correspond to one of the plurality of engagement projecting portions 213 and one of the plurality of bosses 214 has been described in the above embodiment, but this is a non-limiting example. In one or more embodiments disclosed herein, the dedicated hole may correspond to one of the plurality of driving members (i.e., rotating drive sections).

An example in which six insertion through holes 91 are formed in the upper surface portion 9a has been described in the above embodiment, but this is a non-limiting example. In one or more embodiments, one to five, or seven or more insertion through holes may be formed.

An example in which the number of the plurality of engagement projecting portions 213 is five has been described in the above embodiment, but this is a non-limiting example. In one or more embodiments, two to four, or six or more engagement projecting portions may be provided.

An example in which the number of the plurality of bosses 214 is two has been described in the above embodiment, but this is a non-limiting example. In one or more embodiments, three or more bosses may be provided.

An example in which the number of the plurality of driving members 212 is four has been described in the above embodiment, but this is a non-limiting example. In one or more embodiments, two to three, or five or more driving members (rotating drive sections) may be provided.

An example in which the upper surface portion 9a and the side surface portion 9b of the resin molded member 9 form approximately a circular truncated cone shape when viewed from the X1 direction has been described in the above embodiment, but this is a non-limiting example. In one or more embodiments, the shape may be any shape as long as the portions 9a and 9b are fitted to the shape of the attachment portion of the robot arm, and may be a columnar shape or the like.

An example in which the length L1 of the side surface portion 9b along the vertical direction is one sixth (⅙) or more and a half (½) or less of the maximum length L2 of the upper surface portion 9a in the X direction (Y direction) has been described in the above embodiment, but this is a non-limiting example. In one or more embodiments, the length of the side surface portion along the vertical direction may be less than one sixth (⅙) or greater than a half (½) of the maximum length of the upper surface portion in the X direction (Y direction).

An example in which the number of the plurality of insertion through holes 91 is less than the total number of the plurality of driving members 212, the plurality of engagement projecting portions 213, and the plurality of bosses 214 has been described in the above embodiment, but this is a non-limiting example. In one or more embodiments, the number of the plurality of insertion through holes may be the same as the total number of the plurality of driving members, the plurality of engagement projecting portions, and the plurality of bosses.

An example in which the plurality of insertion through holes 91 includes both of the shared hole 92 and the dedicated hole 93 has been described in the above embodiment, but this is a non-limiting example. In one or more embodiments, the plurality of insertion through holes may include only the shared holes, or only the dedicated holes.

An example in which the flexible film member 8 is attached to the proximal end portion 217 of the robot arm 21 by the attachment tool 1 has been described in the above embodiment, but this is a non-limiting example. In one or more embodiments, the flexible film member may be attached to any portion of the robot arm other than the proximal end portion by the attachment tool.

An example in which the first shared hole 92a corresponds to the first driving member 212a toward the X1 direction and the second engagement projecting portion 213b toward the X1 direction, and the second shared hole 92b corresponds to the first driving member 212a toward the X2 direction and the second engagement projecting portion 213b toward the X2 direction has been described in the above embodiment, but this is a non-limiting example. In one or more embodiments, the upper surface portion may be provided with a shared hole that corresponds to both of: the first driving member toward the X1 direction and the second engagement projecting portion toward the X1 direction; and the first driving member toward the X2 direction and the second engagement projecting portion toward the X2 direction.

The invention claimed is:

1. A sterile drape to be attached to an attachment portion of a robot arm used in a robotic surgical system, via an adapter for attachment of a surgical instrument, the sterile drape comprising:
   a flexible film member including a first opening and a second opening and configured to cover the robot arm received through the second opening; and
   a resin molded member configured to close the first opening of the flexible film member,
   wherein the resin molded member includes: an upper surface portion having a shape and a size fitted to an attachment surface of the attachment portion; a side surface portion extending downward from the upper surface portion; and a projection which projects outward from a lower edge of the side surface portion and to which the flexible film member is welded, the upper surface portion, the side surface portion, and the projection being integrally formed,
   wherein the upper surface portion has a plurality of holes at positions corresponding to a plurality of rotating drive sections and a plurality of engagement projecting portions, the rotating drive sections and the engagement projecting portions being formed in the attachment portion, and
   wherein the adapter includes a plurality of rotated members which correspond to the plurality of rotating drive sections, and a plurality of engagement recesses which engage with the plurality of engagement projecting portions; wherein the plurality of holes include a shared hole which corresponds to both at least one of the plurality of rotating drive sections and at least one of the plurality of engagement projecting portions.

2. The sterile drape of claim 1, wherein the side surface portion of the resin molded member has a size and a shape corresponding to an attachment side surface extending downward from the attachment surface.

3. The sterile drape of claim 1, wherein the resin molded member has a circular truncated cone shape.

4. The sterile drape of claim 1, wherein a length of the side surface portion along a vertical direction is one sixth (⅙) or more and a half (½) or less of a maximum length of the upper surface portion in a horizontal direction.

5. The sterile drape of claim 1, wherein the number of the plurality of holes is less than a total number of the plurality of rotating drive sections and the plurality of engagement projecting portions.

6. The sterile drape of claim 5, wherein the plurality of holes include a dedicated hole which corresponds to one of the plurality of rotating drive sections or one of the plurality of engagement projecting portions.

7. The sterile drape of claim 1, wherein the flexible film member is attached to a proximal end portion of the robot arm by an attachment tool at a position of the flexible film member closer to the second opening than to the first opening.

8. An instrument attachment set for attaching a surgical instrument to an attachment portion of a robot arm in a robotic surgical system, the instrument attachment set comprising:
   an adapter including a plurality of rotated members which correspond to a plurality of rotating drive sections provided in the attachment portion, and a plurality of engagement recesses which correspond to a plurality of engagement projecting portions provided in the attachment portion; and
   a sterile drape including: a flexible film member including a first opening and a second opening and configured to cover the robot arm received through the second opening; and a resin molded member configured to close the first opening of the flexible film member,
   wherein the resin molded member includes: an upper surface portion having a shape and a size fitted to an attachment surface of the attachment portion; a side surface portion extending downward from the upper surface portion; and a projection which projects outward from a lower edge of the side surface portion and to which the flexible film member is welded, the upper surface portion, the side surface portion, and the projection being integrally formed, and
   wherein the upper surface portion has a plurality of holes which are disposed at positions that allow engagement between the plurality of rotating drive sections and the plurality of rotated members and engagement between the plurality of engagement projecting portions and the plurality of engagement recesses; wherein the plurality of holes include: a shared hole which corresponds to both of at least one of the plurality of rotating drive sections and at least one of the plurality of engagement projecting portions; and a dedicated hole which corresponds to one of the plurality of rotating drive sections or one of the plurality of engagement projecting portions.

9. The instrument attachment set of claim 8, wherein the side surface portion of the resin molded member has a size and a shape corresponding to an attachment side surface extending downward from the attachment surface.

10. The instrument attachment set of claim 8, wherein the resin molded member has a circular truncated cone shape.

11. The instrument attachment set of claim 8, wherein a length of the side surface portion along a vertical direction is one sixth ($\frac{1}{6}$) or more and a half ($\frac{1}{2}$) or less of a maximum length of the upper surface portion in a horizontal direction.

12. The instrument attachment set of claim 8, wherein the number of the plurality of holes is less than a total number of the plurality of rotating drive sections and the plurality of engagement projecting portions.

* * * * *